United States Patent [19]

Waszmer

[11] 4,100,522

[45] Jul. 11, 1978

[54] CIRCUIT BREAKER WITH ADJUSTABLE SETTING

[76] Inventor: Jacob Waszmer, 15 E. Bedell St., Freeport, N.Y. 11520

[21] Appl. No.: 744,163

[22] Filed: Nov. 22, 1976

[51] Int. Cl.$^2$ .................... A01H 61/08

[52] U.S. Cl. .................... 337/68; 337/94

[58] Field of Search .................... 337/67, 79, 82, 84, 337/94, 349, 360, 361, 376, 68, 37, 38

[56] References Cited

U.S. PATENT DOCUMENTS

| | | | |
|---|---|---|---|
| 3,193,647 | 7/1965 | Beaudoin et al. | 337/68 X |
| 3,240,906 | 3/1966 | Huffman | 337/82 X |
| 3,386,061 | 5/1968 | Delafrange | 337/68 X |
| 3,422,384 | 1/1969 | Filchak et al. | 337/68 X |
| 3,710,294 | 1/1973 | Dries | 337/68 |

*Primary Examiner*—George Harris

*Attorney, Agent, or Firm*—Erwin S. Teltscher

[57] ABSTRACT

A circuit breaker which has an adjustable setting includes a first pair of bars for connecting the circuit breaker to a current supply, and a second pair of bars for connecting it to a load. The circuit-breaker current-supply connecting bars are normally in contact with the circuit-breaker load-connecting bars, and one of the pairs of bars is adapted to be released from contact with the other pair of bars at a predetermined release point upon the application of a predetermined amount of heat to the pairs of bars. An adjustment device is provided for varying the release point of the one pair of bars from the other pair of bars, so that upon a predetermined current passing through the pair of bars, the one pair of bars is heated to the predetermined amount of heat and released from contact with the other pair of bars.

10 Claims, 3 Drawing Figures

CIRCUIT BREAKER WITH ADJUSTABLE SETTING

BACKGROUND OF THE INVENTION

1. Field of the Invention

The field of the invention relates to a circuit breaker with an adjustable setting.

2. Description of the Prior Art

Breakers are known which break the circuit upon a predetermined current passing through the circuit breaker; there are also known fuses which blow upon a current passing therethrough reaching a predetermined current. Whereas the circuit breaker trips and can be reset, the fuse must be replaced. It is relatively easy to change the rating of the fuse, so as to put differently rated fuses for respective different loads in a circuit, according to requirements; it is not, however, been possible hitherto to employ a circuit breaker which can be reset for various load currents.

OBJECT OF THE INVENTION

It is, accordingly, an object of my invention to devise a circuit breaker which has the advantages of a fuse, by its rating being easily changeable, without having the disadvantages of the fuse, i.e. that it cannot be reset, or of the conventional circuit breaker, whose rating cannot be changed.

SUMMARY OF THE INVENTION

I accordingly provide a circuit breaker which has an adjustable setting and which includes means for connecting the circuit breaker to a current supply, means for connecting the circuit breaker to a load, and where the circuit-breaker current-supply connecting-means is normally in contact with the circuit-breaker load-connecting means. One of the circuit-breaker means is adapted to be released from contact with the other of the circuit-breaker means at a predetermined release point upon the application of a predetermined amount of heat to the circuit-breaker means. I additionally provide adjustment means for varying the release point of one of the circuit-breaker means from the other circuit-breaker means so that upon a predetermined current passing through the circuit-breaker means, one of the circuit-breaker means is heated to the predetermined amount of heat and released from contact with the other circuit-breaker means.

The circuit-breaker current-supply connecting-means includes a first pair of conductive bars and the circuit-breaker load connecting-means includes a second pair of conductive bars, each bar of at least one of the pairs of bars including first and second juxtaposed metal strips having different respective coefficients of thermal expansion, so that, upon the predetermined current passing through the circuit-breaker means, one of the pair of contact bars is disengaged from the other pair of contact bars through the different rate of thermal expansion of the first and second metal strips.

I additionally provide a housing for receiving the pair of bars, and the release-point adjustment means include pressure means for exerting pressure on one of the pairs of bars to vary contact pressure between the latter and the other pair of bars.

The contact-pressure means includes a non-conductive bar or the like, which is slidably arranged within the housing and normally rests on the one of the pair of bars for exerting an adjustable pressure on the latter.

The contact-pressure means additionally include a threaded shaft which is rotatably disposed in the housing and a spring-loaded rod attached at substantially right angles to the non-conductive bar and formed with a threaded opening for receiving the threaded shaft. A predetermined rotation of the shaft then causes a predetermined pressure to be exerted by the non-conductive bar upon the one of the pair of bars.

A knurled knob may be attached to the threaded shaft and disposed external to the housing for effecting the predetermined rotation.

In a preferred version of my invention, I additionally provide means for preventing the one of the circuit-breaker means from re-establishing contact with the other of the circuit-breaker means upon the application of the predetermined amount of heat, and resetting means for resetting the circuit-breaker means for resuming normal contact with one another.

The contact-prevention means preferably includes spring-loaded wedge means releasably attached to the housing for moving from an initial position to a position interposed between the circuit-breaker means upon the one of the circuit-breaker means being released from contact with the other of the circuit-breaker means; the resetting means include a retractable handle attached to the wedge means for manually resetting the wedge means to the initial position upon the predetermined current having ceased to pass through the circuit-breaker means.

The circuit-breaker current-supply means preferably includes a first pair of contacts and the circuit-breaker load-connecting means preferably includes a second pair of contacts normally in contact with the first pair of contacts; the contact-prevention means preferably include a compression spring for urging the wedge means to exert pressure against the first and second pair of contacts when in contact with one another.

An electrically actuable light source is preferably connected to the circuit-breaker load-connecting means.

BRIEF DESCRIPTION OF THE DRAWING

My invention will be better understood with reference to the accompanying drawing in which.

DESCRIPTION OF THE PREFERRED EMBODIMENT

Figure 1:
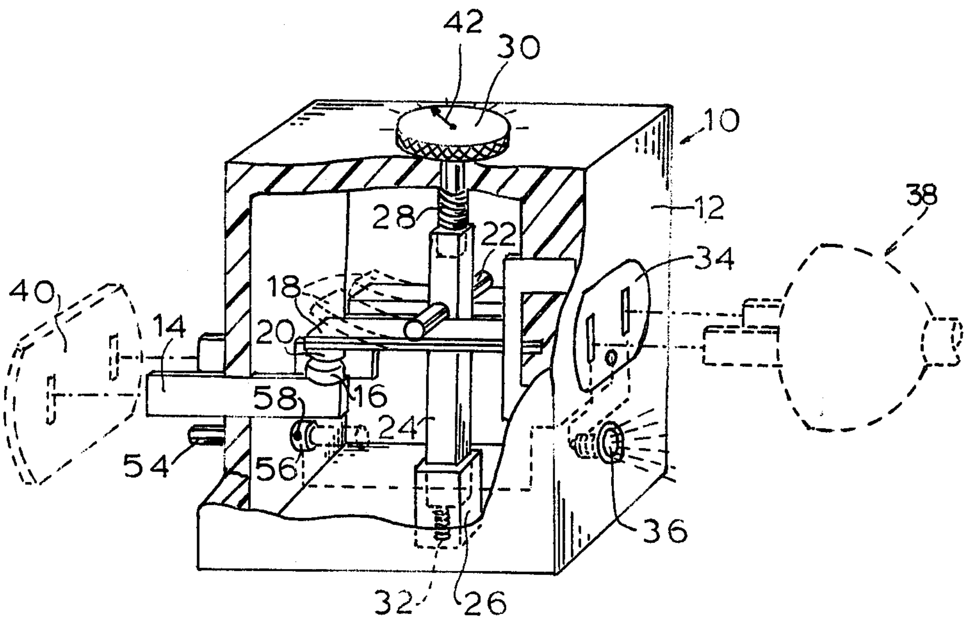
FIG. 1 shows a perspective view of the circuit-breaker having an adjustable setting, in part-section, according to my invention.

Referring now to the drawing, a circuit-breaker or circuit-breaker adapter 10 includes a housing 12, a plug defining first pair of bars 14 provided at one end thereof with contacts 16, only one contact being shown for clarity's sake, and a second pair of bars 18 provided with second pairs of contacts 20. The contacts 16 and 20 normally make contact with one another. The bars 14 and 18 are made of metal. A non-conductive bar 22 is fitted into a holder 24 which is slidable within a projection 26 mounted in the housing 12. A threaded shaft 28 is rotatably disposed in the housing 12, and has a knurled knob 30 attached thereto. The rod 24 is internally threaded on at least one end thereof so as to receive the threaded shaft 28. When the knurled knob 30 is rotated clockwise, the non-conductive bar 22 proceeds in a downward direction as seen in FIG. 1, thus exerting additional pressure on the bars 18; the threaded shaft 28 moves against the force of a compression spring 32, normally urging the rod 24 to move in a direction urging opening of the contacts 16 and 20. The bars 18 are electrically connected to a socket 34 disposed within the housing 12, and the socket 34 is connected to an electrically actuable light source 36. A standard plug 38 fits into the socket 34, and the metal bars 14 may be plugged into a standard socket 40 from which current can be drawn.

The operation of the circuit-breaker, according to my invention, is as follows: the knurled knob 30 is first set for a desired release point by turning the dial pointer 42 of the knob 30 to a desired setting on a scale engraved on the housing 12. Calibration of the circuit-breaker may be effected by passing a predetermined current through connecting an appropriate load to the circuit-breaker, and then turning the knurled knob 30 in a counter-clockwise direction until the pilot light 36 goes out. The knurled knob 30 is then turned back one setting or one notch of the scale in a clockwise direction, when the pilot light will be seen to come on again. It is preferable to wait a few seconds before turning the knob 30 clockwise, to allow the contacts 18 to cool off, the circuit-breaker 10 being adjusted to an arbitrary safety margin, for example, ½ of an ampere.

Figure 2:
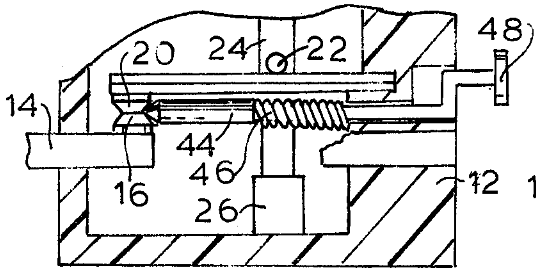
FIG. 2 is a fragmentary sectional view of the contact-prevention means of the circuit-breaker, when the circuit-breaker contacts are closed.
Figure 3:
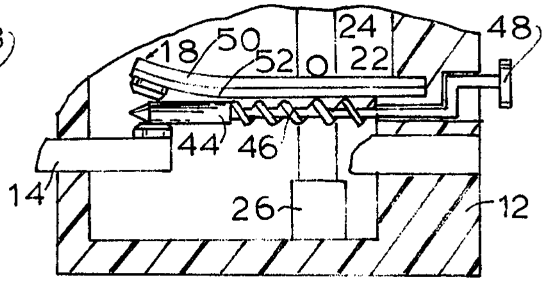
FIG. 3 corresponds to FIG. 2, but with the contacts open and the contact-prevention means interposed between the contacts.

In a preferred version of my invention, best seen in FIGS. 2 and 3, a wedge 44 is urged by a compression spring 46 to exert pressure against the normally closed contacts 20 and 16. When the contacts 20 and 16 are opened due to the current through the circuit-breaker exceeding the predetermined current, the wedge 44 exerts a forward motion, inserting itself between the contacts 16 and 20, as the result of the compression spring 46 forcing it to slide between the contacts 16 and 20. When a fault in the load causing the circuit-breaker to trip has been removed, a reset tab 48 can be pulled in an outward direction to reset the circuit-breaker to its initial position shown in FIG. 2. Each of the metal bars 18 consists of a first metal strip 50 and a second metal strip 52, having different respective coefficients of thermal expansion. The different coefficients of thermal expansion of the metal strips 50 and 52 cause the bar 18 to bend in an outward direction when it is exposed to a predetermined amount of heat, as shown in FIG. 3, and also as shown dotted in FIG. 1. A prong 54 is retractably mounted within the circuit-breaker 10 and can be clamped tight in an extended position, shown in full lines, or in a retracted position, shown in dotted lines, to a clamping ring 56, by means of an adjustment screw 58 disposed in the clamping ring 56.

The foregoing is considered as illustrative only of the principles of the present invention; since numerous modifications and changes will readily occur to those skilled in the art, it is not intended to limit the invention to the exact construction and operation shown and described, the appended claims encompassing any suitable modifications and equivalents of the present invention.

What is claimed is:

1. A circuit breaker having an adjustable setting comprising:

plug means for connecting the circuit breaker to a current supply;

socket means for connecting the circuit breaker to a load, the circuit-breaker current-supply connecting-means being normally in contact with the circuit-breaker load-connecting means, one of said circuit-breaker means being adapted to be released from contact with the other of said circuit-breaker means at a predetermined release point upon the application of a predetermined amount of heat to said circuit-breaker means; and adjustment means for varying the release point of said one of said circuit-breaker means from the other of said circuit-breaker means, whereby, upon a predetermined current passing through said circuit-breaker means, said one of said circuit-breaker means is heated to said predetermined amount of heat and released from contact with the other of said circuit-breaker means.

2. A circuit breaker according to claim 1 wherein said circuit-breaker current-supply connecting-means comprise a first pair of conductive bars, and said circuit-breaker load-connecting means comprise a second pair of conductive bars, each bar of at least one of said pairs of bars comprising first and second juxtaposed metal strips having different respective coefficients of thermal expansion, whereby, upon the predetermined current passing through said circuit-breaker means one of said pair of contacts bars is disengaged from said other pair of contact bars through the different rate of thermal expansion of said first and second metal strips.

3. A circuit breaker according to claim 1 further comprising a housing for receiving said pairs of bars, and wherein the release-point adjustment means comprise pressure means for exerting pressure on said one of said pairs of bars to vary contact pressure between the latter and said other pair of bars.

4. A circuit breaker according to claim 3 wherein said contact pressure means comprises a non-conductive bar slidably arranged within said housing and normally resting on said one of said pair of bars for exerting an adjustable pressure on said one of said pair of bars.

5. A circuit breaker according to claim 4 wherein said contact pressure means further comprises a threaded shaft rotatably disposed in said housing, and a spring-loaded rod attached substantially at right angles to said non-conductive bar and formed with a threaded opening for receiving said threaded shaft, whereby a predetermined rotation of said shaft causes a predetermined pressure to be exerted by said non-conductive bar upon said one of said pair of bars.

6. A circuit breaker according to claim 4 further comprising a knurled knob attached to said threaded shaft and disposed external to said housing for effecting said predetermined rotation.

7. A circuit breaker according to claim 1 further comprising means for preventing said one of said circuit-breaker means from re-establishing contact with said other of said circuit-breaker means upon the application of said predetermined amount of heat, and resetting means for resetting said circuit-breaker means for resuming normal contact with one another.

8. A circuit breaker according to claim 7 wherein the contact-prevention means comprise spring-loaded wedge means releasably attached to said housing for moving from an initial position to a position interposed between said circuit-breaker means upon said one of said circuit-breaker means being released from contact with said other of said circuit-breaker means, and wherein said resetting means comprises retractable tab means attached to said wedge means for manually resetting said wedge means to the initial position upon the predetermined current having ceased to pass through said circuit-breaker means.

9. A circuit breaker according to claim 8 wherein said circuit-breaker current-supply means includes a first pair of contacts, and said circuit-breaker load-connecting means includes a second pair of contacts normally in contact with said first pair of contacts, and said contact-prevention means includes a compression spring for urging said wedge means to exert pressure against said first and second pair of contacts when the latter are in contact with one another.

10. A circuit breaker according to claim 1 further comprising an electrically actuable light source connected to said circuit-breaker load-connecting means.

* * * * *